(12) United States Patent
Wuttke et al.

(10) Patent No.: US 6,635,672 B1
(45) Date of Patent: Oct. 21, 2003

(54) AGENT FOR LOWERING PROLACTIN

(75) Inventors: Wolfgang Wuttke, Bovenden (DE); Hubertus Jarry, Neu-Eichenberg (DE); Michael Popp, Lauf/Pegnitz (DE); Volker Christoffel, Sengenthal (DE); Barbara Spengler, Neumarkt/Opf. (DE)

(73) Assignee: Bionorica AG, Neumarkt/Opf (DE)

( * ) Notice: Subject to any disclaimer, the term of this patent is extended or adjusted under 35 U.S.C. 154(b) by 0 days.

(21) Appl. No.: 09/856,219

(22) PCT Filed: Nov. 5, 1999

(86) PCT No.: PCT/EP99/08507
§ 371 (c)(1), (2), (4) Date: Sep. 24, 2001

(87) PCT Pub. No.: WO00/30623
PCT Pub. Date: Jun. 2, 2000

(30) Foreign Application Priority Data

Nov. 19, 1998 (DE) .......................... 198 53 476

(51) Int. Cl.[7] ..................... A61K 31/34; A61K 31/045; C07C 33/14

(52) U.S. Cl. ................. 514/461; 514/510; 514/546; 514/691; 514/715; 514/729; 568/619

(58) Field of Search ................... 514/461, 546, 514/510, 691, 729, 715; 568/819

(56) References Cited

FOREIGN PATENT DOCUMENTS

| WO | WO 96/24684 | 8/1996 |
|---|---|---|
| WO | WO 99/63978 | 12/1999 |

OTHER PUBLICATIONS

Rudi et al, J. of Natural Products, 1992, vol. 55, No. 10, pp. 1408–1414.*
Misra et al, Tet. Letters, 1968, No. 22, pp. 2685–2686.*
International Search Report, PCT/EP99/08507, International Filing Date May 11, 1999.
German Search Report, DE 198 53 476.0, Mai 26 1999.
XP–000913717, Sliutz, G. et al., *Agnus Castus Extracts Inhibit Prolactin Secretion of Rat Pituitary Cells*, Hormone and Metabolic Research., vol. 25, pp. 253–255 (1993).
XP–000913700, Milewicz, A. et al., (*Vitex agnus castus–Extrakt zur Behandlung von Regeltempoanomalien infolge latenter Hyperprolaktinämie, Ergebnisse einer randomisierten Plazebo–kontrollierten Doppelblindstudie* (*Vitex agnus castus extract in the treatment of luteal phase defects due to latent hyperprolactinaemia: Results of a randomized placebo–controlled double blind study*), Arzneimettel–Forschung, vol. 43, No. 7, pp. 752–756 (1993).
XP–000913660—Cahill, D. J. et al., *Multiple follicular development associated with herbal medicine*, Human Reproduction, vol. 9, No. 8, pp. 1469–1470 (1994).

XP–000913600– Ohsaki, Ayumi et al., *The Isolation and in vivo Potent Antitumor Activity of Clerodane Diterpenoid from the Oleoresin of the Brazilian Medicinal Plant, Copaifera Langsdorfii Desfon*, Bioorganic & Medical Chemistry Letters, vol. 4, No. 24, pp. 2889–2892 (1994).

(List continued on next page.)

*Primary Examiner*—Bernard Dentz
(74) *Attorney, Agent, or Firm*—Sidley Austin Brown & Wood LLP

(57) ABSTRACT

The present invention relates to a prolactin lowering drug containing at least one bicyclic diterpene of the labdane or clerodane type:

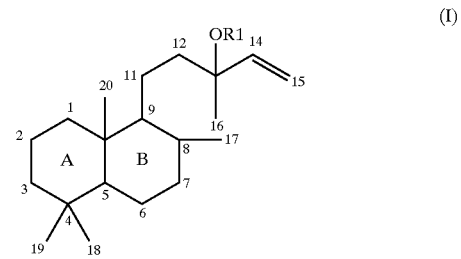

(I)

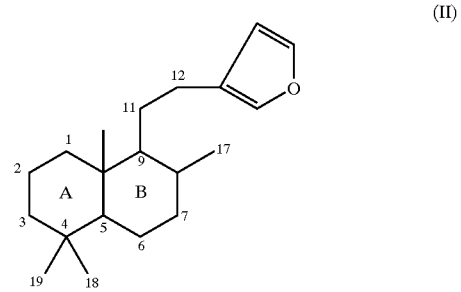

(II)

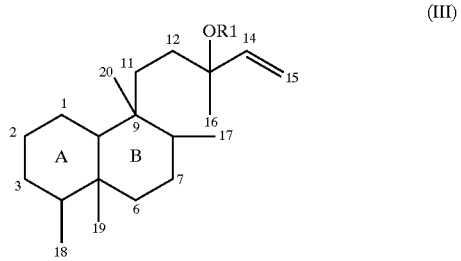

(III)

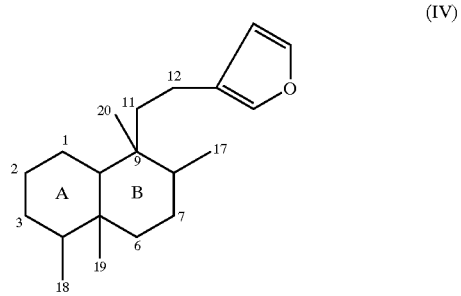

(IV)

Figure 1:
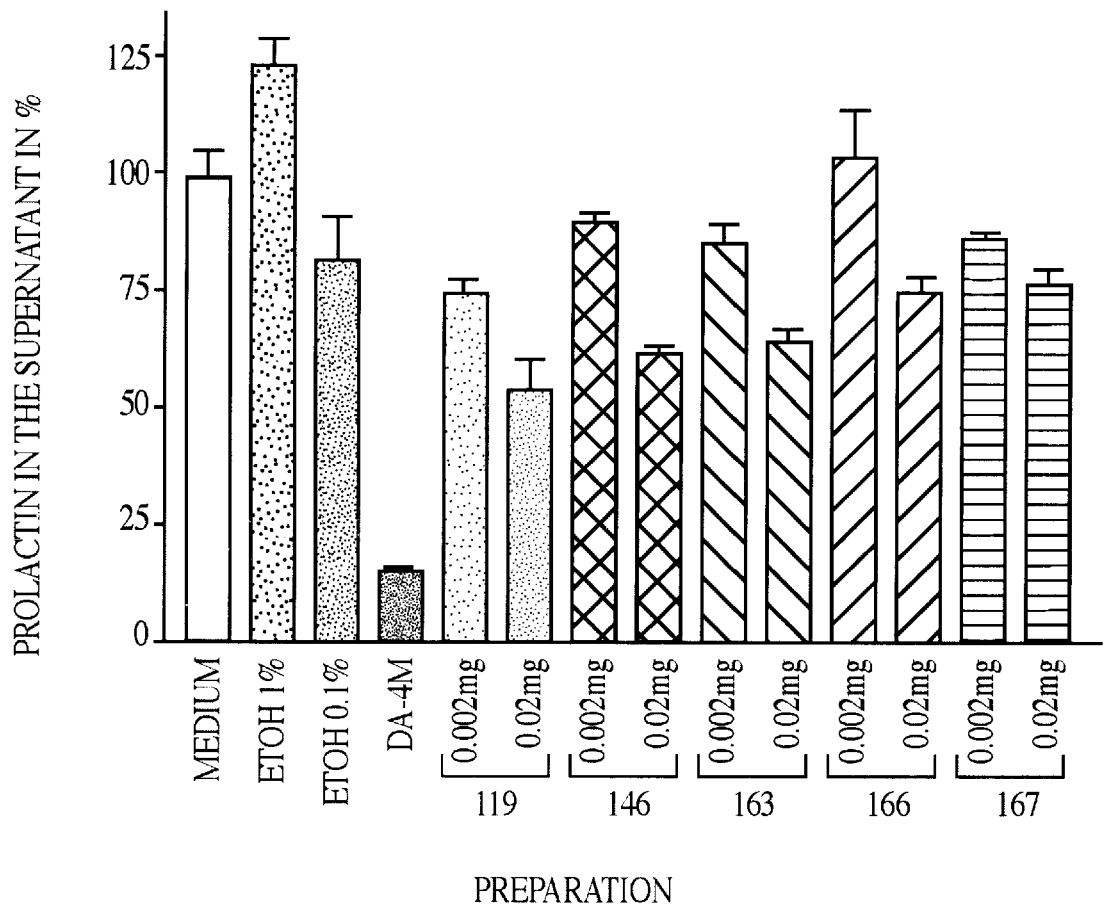

wherein R1=H, $C_1$ to $C_3$ alkyl or $C_1$ to $C_3$ acyl.

12 Claims, 1 Drawing Sheet

OTHER PUBLICATIONS

XP-000913598, Chen, Zhen-Ping et al., *Studies on the Anti-Tumour, Anti-bacterial, and Wound-Healing Properties of Dragon's Blood*, Planta Med., vol. 60, pp. 541–545 (1994).

XP-000913597, Rojas, A. et al., *Smooth Muscle Relaxing Compounds from Dodonaea viscosa*, Planta Medica, vol. 62, pp. 154–159 (1996).

XP-000913581, Jarry, H. et al., *In vitro prolactin but not LH and FSH release is inhibited by compounds in extracts of Agnus castus: direct evidence for a dopaminergic principle by the dopamine receptor assay*, Exp. Clin. Endocrinol., vol. 102, pp. 448–454 (1994).

XP-000907424, Han, Byung Hoon et al., *In Vitro Platelet Activating Factor Receptor Binding Inhibitory Activity of Pinusolide Derivatives: A Structure—Activity Study*, J. Med. Chem., vol. 41, pp. 2626–2630 (1998).

XP-000907423, Males, Z. et al., *Composition of the essential oil of Vitex agunus–castus L. f. rosea fruits*, Pharmazie, vol. 53, pp. 728–729 (1998).

XP-000907422, Taguchi, Heihachiro, *Studies on the Constituents of Vitex cannabifolia*, Chem. Pharm. Bull., vol. 24, No. 7, pp. 1668–1670 (1976).

Costa, Marta et al., *Assignment of $^{13}C$ NMR data of methyl (+)–hardwickiate and its derivatives*, IN: Magn. Reson. Chem., Vol 36, pp. 542–544 (1998), Magn. Reson. Chem. 36:542–544 (1998).

McChesney, J. D. et al., *Ent–Clerodanes of Croton Sonderianus*, In: Fitoerapia, Bol. LXI, No. 1, pp. 172–175 (1990).

XP-000907421, Kondo, Yoshikazu et al., *Studies on the Constituents of Vitex rotundifolia L. fil.*, Chem. Pharm. Bull., vol. 34, No. 11, pp. 4829–4832 (1986).

Chemical Abstracts, vol. 95, Ref. 115786q.

* cited by examiner

AGENT FOR LOWERING PROLACTIN

This application is a 371 of PCT/EP99/08507 filed Nov. 19, 1999.

The present invention relates to prolactin lowering drugs.

Extracts from Vitex agnus-castus (agnus castus, chaste tree) have been used for long in the medicine of natural remedies for treatment of the premenstrual syndrome. Shortly prior to menstruation, patients frequently complain of tenseness in the breasts, clinically accompanied by an elevated prolactin content.

Extracts from Vitex agnus-castus possess prolactin lowering properties which could furthermore be ascertained clinically and pharmacologically in the prior art. Attempts have been numerous in the prior art to characterize or even isolate those substances in Vitex agnus-castus that are responsible for an alleviation of the premenstrual sydrome.

Thus the dissertation by Daniel Berger entitled, *"Vitex agnus-castus: Unbedenklichkeit und Wirksamkeit beim prämenstruellen Syndrom, Wirkprinzipien and Wirkmechanismen eines neu entwickelten Extraktes"* [Vitex agnus-castus: Recognized safety und effectivity in the premenstrual syndrome, effective principles and mechanisms of a newly developed extract] at the Faculty of Philosophy and Natural Science of Basle University, of Jan. 13, 1998 deals with a multiplicity of aspects brought into connection with Vitex agnusastus.

This dissertation describes a number of different constituents which were taken into consideration for an explanation of the pharmacological properties of the drug.

Thus in Vitex agnus-castus the iridoid glycosides aucubin, agnuside and eurostoside are found both in the leaf drug and in the fruit drug.

Moreover the lipophilic flavonols casticin, penduletin, chrysosplenol D and the 3,6,7,4'-tetramethyl ether of 6-hydroxykaempferol could be isolated from the fruit.

The prior art furthermore describes that progesterone, 17α-hydroxy-progesterone, testosterone and epitestosterone could be detected in the fruit of Vitex agnus-castus.

Apart from this, a total of about 73 different compounds can be found in the fruit of Vitex agnus-castus, above all monoterpenes such as α-pinene, sabinene, β-phellandrene and 4-terpineol, and sesquiterpenes such as β-caryophyllene, allo-aromadendrene, germacrene B, spathulenol and τ-cadinol.

Besides the classes of substances already mentioned above, considerable amounts of fatty-acids can moreover be found in the fruit of Vitex agnus-castus, as there are saturated, monounsaturated and polyunsaturated fatty acids. Thus, e.g., α-linolenic acid, oleic acid, stearic acid, palmitic acid, linoleic acid and adrenic acid were detected in the fruit.

Further examination of the essential oil from the fruit of Vitex agnus-castus also uncovered the presence of diterpenes. The above mentioned dissertation provides information that the following diterpenes were isolated from the fruit of Vitex agnus-castus:

rotundifuran, vitexilactone and 6β,7β-diacetoxy-13-hydroxy-labda-8,14-diene, the structural formulae of which are represented hereinbelow:

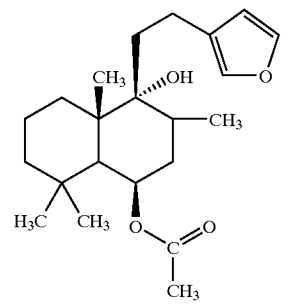

Rotundifuran

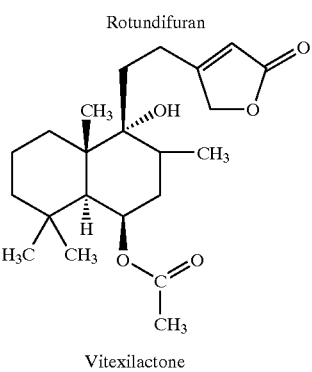

Vitexilactone

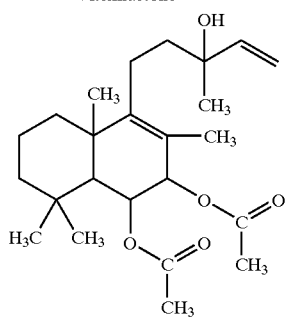

6β, 7β-Diacetoxy-13-hydroxy-labda-8, 13-diene

In this prior art a multiplicity of testing processes were performed in order to find out about the effective mechanisms of extracts from Vitex agnus-castus, and whether a particular substance or a particular class of substances is suited for explaining the pharmacological effects of the full extract.

Thus, e.g., measurements were carried out on the various opioid receptors, on the benzodiazepin receptor, on the serotonin reuptake site, on the histamine-$H_1$ receptor and on the dopamine-$D_2$ receptor.

In order to verify the results of the receptor binding studies on the dopamine-$D_2$ receptor with fractions from Vitex agnus-castus and thereby find the actual active substances, experimentation was carried out in the above described prior art with the known constituents of Vitex agnus-castus (pure substances). These pure constituents were aucubin, casticin, homoorientin, linoleic acid, luteolin-7-glycoside, orientin and the diterpenes vitexin, rotundifuran, 6β,7β-diacetoxy-13-hydroxy-labda-8,14-diene.

The dissertation does, however, explicitly state on page 154 in Chapter 2.3.4.5 that none of the tested substances had a sufficiently low $IC_{50}$ value for being able to exaplain, as a single substance, the activity and thus the pharmacological effects of the full extract or of a lipophilic hexane fraction from Vitex agnus-castus.

Starting out from this prior art, it was an object of the present invention to provide pure substances from the fruit of Vitex agnus-castus, whereby a drug for treating the premenstrual syndrome may be produced in pharmaceutical formulation.

This object is attained by a drug in accordance with claim 1 and by the novel substances in accordance with claim 12 and claim 14.

In the framework of the present invention it was surprisingly found that compounds from the class of bicyclic diterpenes have a prolactin lowering effect on cultivated pituitary cells from rats. It is highly likely that this mechanism can be transferred to humans.

Herein the effective diterpenes may have a skeletal structure both of the labdane type and of the clerodane type:

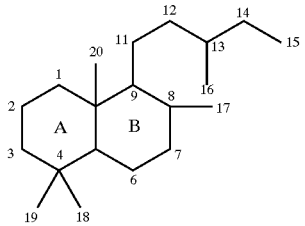

Labdane structure

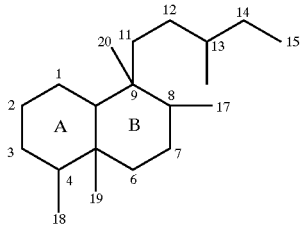

Clerodane structure

In particular it was found that a prolactin lowering effect on cultivated pituitary cells may be achieved with compounds in accordance with the following general formulae I to IV with, at the same time, low cytotoxicity:

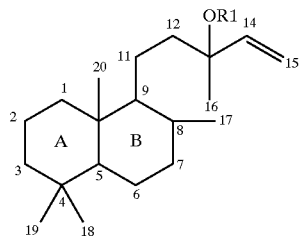
(I)

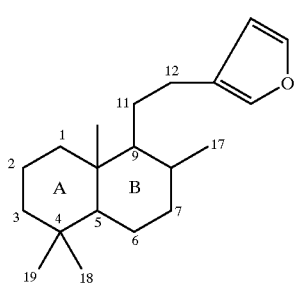
(II)

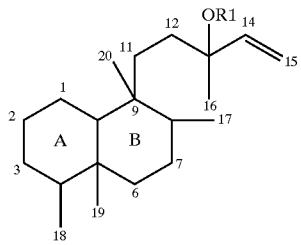
(III)

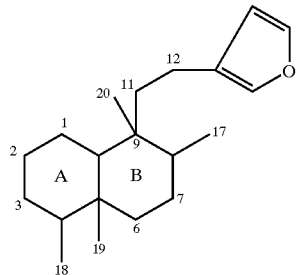
(IV)

with R1=H, C1 to C3 alkyl or C1 to C3 acyl;

wherein the rings A and/or B in the case of general formulae (I) or (II) are optionally substituted in position 1, 2, 3, 4, 6, 7, 8 or 9 with at least one OX radical, with X=H, $C_1$ to $C_3$ alkyl or $C_1$ to $C_3$ acyl;

wherein the rings A and/or B in the case of general formulae (III) or (IV) are optionally substituted in position 1, 2, 3, 4, 6, 7, or 8 with at least one OX radical, with X=H, $C_1$ to $C_3$ alkyl or $C_1$ to $C_3$ acyl;

wherein optionally at least one carbon atom in positions 17, 18, 19 and 20 is substituted with an OX radical, with X=H, $C_1$ to $C_3$ alkyl or $C_1$ to $C_3$ acyl;

wherein optionally at least one $CH_3$ group in positions 17, 18, 19 and 20 is replaced by a COOH group;

wherein optionally at least one of ring positions 1, 2, 3, 6, or 7 is a keto group; and wherein optionally at least one double bond is present in ring positions 1, 2, 3, 6, 7, 8, 8(17) of formulae (I) and (III); and wherein optionally at least one double bond is present in ring positions 1, 2, 3, 4(18), 6, 7, 8, 8(17) of formulae (II) and (IV).

Moreover the following compounds are preferred embodiments of the present invention:

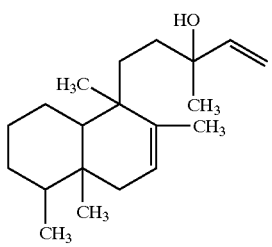

-continued

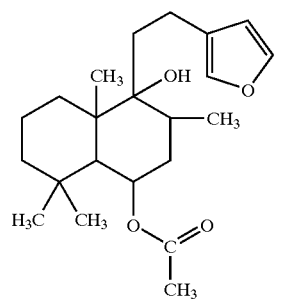
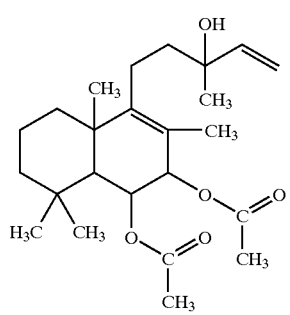
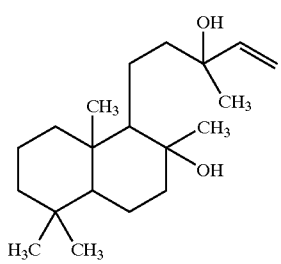
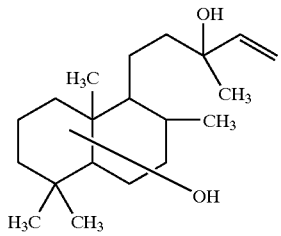
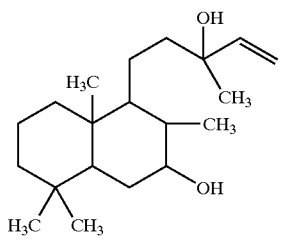
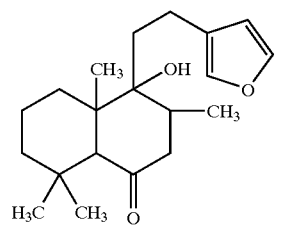

-continued

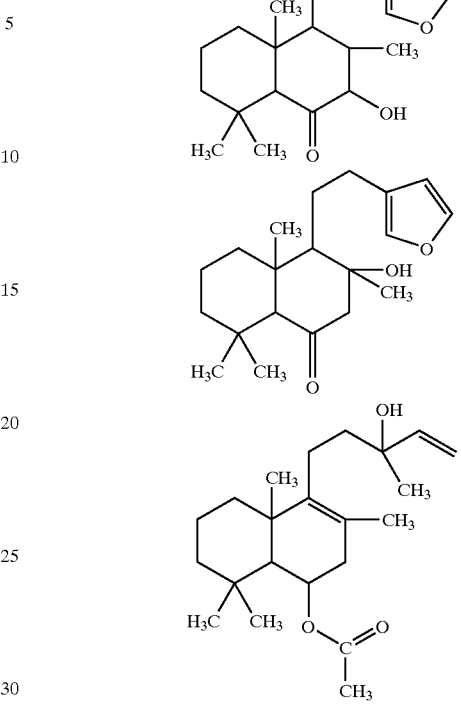

as well as cleroda-Y,14-dien-13-ol, with Y=ring position 1, 2, 3, 4(18), 6, 7 or 8(17); and cleroda-Y,Z,14-trien-13-ol, with Y or Z=ring position 1, 3, or 1, 4(18) or 1, 6 or 1, 7 or 1, 8(17) or ring position 2,4(18) or 2, 6 or 2, 7 or 2, 8(17) or ring position 4(18), 6 or 4(18), 7 or 4(18), 8(17) or ring position 6, 8(17).

It was possible to enrich and characterize the like compounds from an ethanolic-aqueous extract from fruit of Vitex agnus-castus by fractionated lipophilic extraction, and to determine their structures.

In particular extraction with highly lipophilic solvents such as medium-length chain hydrocarbons $C_5$–$C_{10}$, in particular with n-hexane, resulted in strong enrichment of the prolactin lowering effect. Moreover extraction from fruit of Vitex agnus-castus with supercritical carbon dioxide allowed for strong enrichment of the effective principle, which could be reduced to the compounds in accordance with general formulae I to IV.

All of the compounds in accordance with the invention, the structural formulae of which are represented above, exhibit inhibition of the released prolactin on lactotropic cells from rats' pituitary glands.

In separate studies on cytotoxicity it was found that all of the compounds isolated and characterized in accordance with the invention exhibited low cytotoxicity, a fact that renders them particularly attractive in terms of pharmaceutical formulation.

It was furthermore found that the named substances also bind to the human recombinant dopamine-D2 receptor.

Further advantages and features of the present invention result from the description of embodiments and from the drawing, wherein:

FIG. 1 shows the influence of bicyclic diterpenes on prolactin release from cultivated pituitary cells of rats.

An ethanolic extract from Fructus Agni casti is produced in a manner known per se by maceration or percolation with organic solvents or mixtures of organic solvents with water or with supercritical carbon dioxide.

To this end, preferably mixtures of ethanol with water in a ratio of 50:50 to 90:10 at a temperature from 20 to 60 degrees Celsius are used.

The extract obtained in this manner is distributed between two non-miscible phases having different polarities. Herein alkanes, halogenated hydrocarbons, ketones, esters are used as a lipophilic phase, and alcohols and water as a hydrophilic phase. Advantageously identical volumes of C5 to C7 alkanes and ethanol/water mixtures in a ratio of 1:2 to 1:10 are used.

The lipophilic phase contains the prolactin lowering activity and may be further purified with the aid of known methods, such as e.g. high-pressure liquid chromatography and preparative layer chromatography in a manner known per se.

From 1 kg of ground fruit of Vitex Agnus castus an extract is produced by percolation with 10 l of ethanol/water 6/4 (v/v). An inspissated extract produced therefrom and having a dry residue of 1.75 g is distributed between 375 ml of 15% EtOH and 375 ml of n-hexane in the separating funnel, the n-hexane phase is withdrawn, and the aqueous phase is again extracted by shaking with n-hexane.

Following concentration under reduced pressure, the combined hexane phases give a residue of 300 mg.

The residue thus obtained is further separated by means of high-pressure liquid chromatography. For this a column having the dimensions of 21.4×300 mm is used, with C-18 material having a particle size 8 μm as the stationary phase. Chromatography is carried out at a flow of 10 ml/min of a mixture of acetonitrile/water 60/40 as the solvent. Following charging of the sample, the acetonitrile content is linearly increased to 100% within 60 minutes.

All of the diterpenes elute in the volume between 350 and 450 ml. From 300 mg of hexane phase, approx. 38 mg of mixture of diterpenes are obtained. The diterpenes are suitably collected in the form of fractions.

Further purification of the mixture of diterpenes thus obtained is performed by means of preparative layer chromatography on silica gel layers having a layer thickness of 1 mm, with different flow agents in accordance with the description further below for the single substances. Detection is performed with anisic aldehyde reagent (DAB 10, 1997). The zones of the pure diterpenes on the thin-layer plate are eluted with the aid of chloroform/methanol and analyzed by means of coupled gas chromatography mass spectrometry.

Preparation of 98–146 (designated by "146" in FIG. 1): 6β-Acetoxy-9α-hydroxy-15,16-epoxy-13(16),14-labdadiene (rotundifuran);

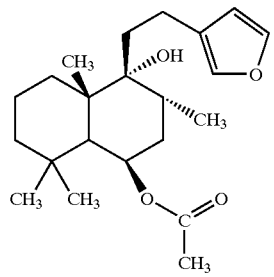

Flow agent: chloroform/methanol 95/5; Rf value: 0.75; Characteristic fragments of the underivatized substance in GC-MS: m/z=362 [M]+, 344, 302, 287, 284, 207, 150, 135, 95, 81.

Preparation of 98–119 (designated by "119" in FIG. 1.): Cleroda-y, 14,-dien-13-ol; Flow agent: chloroform/methanol 95/5; Rf value: 0.63; Characteristic fragments of the underivatized substance in GC-MS: m/z=290 [M]+, 272, 257, 243, 229, 191, 189.

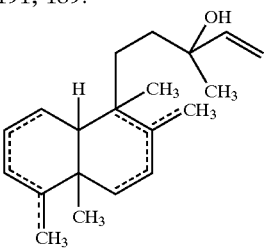

Preparation of 98–153 (not shown in FIG. 1): x, 13-Dihydroxy-14-labdene; Flow agent: chloroform/methanol 95/5; Rf value: 0.37; Characteristic fragments of the underivatized substance in GC-MS: m/z=290 [M-H20]+, 275, 272, 257, 191, 177.

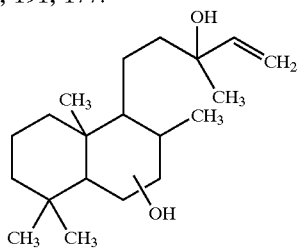

Preparation of 98–152 (not shown in FIG. 1): 6β,7β-Diacetoxy-13-hydroxy-labda-8,14-diene; Flow agent: chloroform/methanol 99/1; Flow distance 16 cm, developed 3×; Rf value: 0.5; Characteristic fragments of the underivatized substance in GC-MS: m/z=346 [M-60]+, 307, 304, 286, 247, 205, 187, 177, 135.

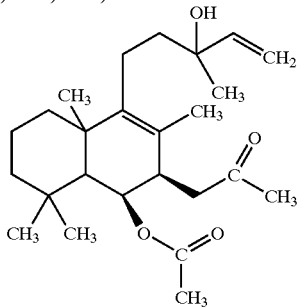

Preparation of 98–166 (designated by "166" in FIG. 1): x-Hydroxy-y-keto-15,16-epoxy-13(16), 14-labdadiene; Flow agent: chloroform/n-hexane 90/10; Develop 3×, flow distance 16 cm; Rf value: 0.74; Characteristic fragments of the underivatized substance in GC-MS: m/z=318 [M]+, 300, 285, 193, 166, 95, 81.

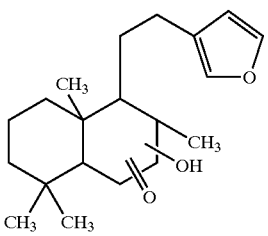

Preparation of 98–167 (designated by "167" in FIG. 1): x-Acetoxy-13-hydroxy-labda-y, 14-diene; Flow agent: chloroform/n-hexane 90/10; Develop 3×, flow distance 16 cm; Rf value: 0.55; Characteristic fragments of the underivatized substance in GC-MS: m/z=330 [M-H20]+ 288, 270, 255, 249, 189, 132, 119, 71.

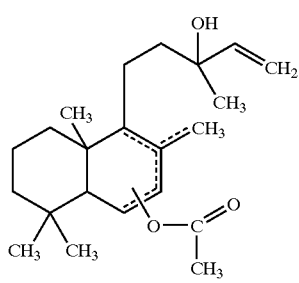

Influence on prolactin release:

Determination of prolactin release from cultivated pituitary cells of male rats was performed as described in Jarry et. al., Experimental and Clinical Endocrinology, Vol.102, (1994) 448–454. The diterpenes were added to the cell cultures in ethanolic solution. The corresponding ethanol concentrations and dopamine were carried along as controls.

The mean value of the measured prolactin concentration of supernatants in cells incubated in unsupplemented medium is set to be equal 100%. The diterpenes significantly lower the release of prolactin. The results are represented in FIG. 1. It shows lowering of prolactin release from cultivated pituitary cells of rats through bicyclic diterpenes. As a control, medium, medium plus ethanol and $10^{-4}$ molar dopamine (=DA–4M) were carried along. The concentration is indicated in mg of diterpene per ml of medium.

What is claimed is:

1. A prolactin lowering drug comprising at least one bicyclic diterpene compound of the clerodane type in accordance with at least one of general formulae (III) or (IV):

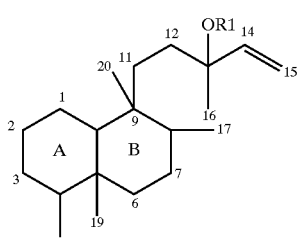
(III)

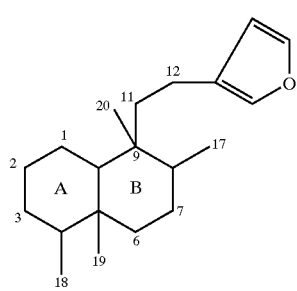
(IV)

wherein $R_1$=H, $C_1$ to $C_3$ alkyl or $C_1$ to $C_3$ acyl;

wherein the rings A and/or B in the case of general formulae (III) or (IV) are optionally substituted in position 1, 2, 3, 4, 6, 7, or 8 with at least one OX radical, with X=H, $C_1$ to $C_3$ alkyl or $C_1$ to $C_3$ acyl;

wherein optionally at least one carbon atom in position 17, 18, 19 and 20 is substituted with an OX radical, with X=H, $C_1$ to $C_3$ alkyl or $C_1$ to $C_3$ acyl;

wherein optionally at least one $CH_3$ group in position 17, 18, 19 and 20 is replaced by one COOH group;

wherein optionally at least one of ring positions 1, 2, 3, 6, or 7 is a keto group; and wherein optionally at least one double bond is present in ring positions 1, 2, 3, 6, 7, 8, 8(17) of formula (III); and wherein optionally at least one double bond is present in ring positions 1, 2, 3, 4(18), 6, 7, 8, 8(17) of formula (IV);

with the exception of the following compounds: (+) hardwickiic acid, crolechinic acid, and hautriwaic acid.

2. A prolactin lowering drug according to claim 1, comprising a compound having the following formula:

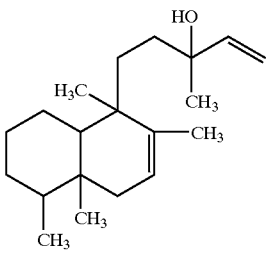

3. Cleroda-Y, 14-dien-13-ol, wherein Y=ring positions 1, 2, 6, 7 or 8(17).

4. Cleroda-Y,Z, 14-trien-13-ol, wherein Y or Z=ring position 1, 3, or 1, 4(18) or 1, 6 or 1, 7 or 1, 8(17) or ring position 2, 4(18) or 2, 6 or 2,7 or 2, 8(17) or ring position 4(18), 6 or 4(18), 7 or 4(18), 8(17) or ring position 6, 8(17).

5. A method of treating premenstrual syndrome, mastodynia, or a disorder of the menstrual cycle in a woman in need of treatment, comprising:

administering a pharmaceutically acceptable formulation comprising the prolactin lowering drug of claim 1 or claim 2, or the compound of claim 3 or claim 4, to the woman in need of treatment.

6. The method of claim 5, wherein the disorder of the menstrual cycle is oligomenorrhea or amenorrhea.

7. A method of lowering prolactin release by a mammalian pituitary cell, comprising:

adding the prolactin lowering drug of claim 1 or claim 2, or the compound of claim 3 or claim 4, to the cell in an amount sufficient to lower the release of prolactin by the cell, compared to a control not receiving the prolactin lowering drug or the compound.

8. A prolactin lowering drug, comprising the compound of claim 3.

9. A prolactin lowering drug, comprising the compound of claim 4.

10. A method of treating premenstrual syndrome, mastodynia, or a disorder of the menstrual cycle in a woman in need of treatment, comprising:

administering a pharmaceutically acceptable formulation comprising the prolactin lowering drug of claim 8 or claim 9, to the woman in need of treatment.

11. The method of claim 10, wherein the disorder of the menstrual cycle is oligomenorrhea or amenorrhea.

12. A method of lowering prolactin release by a mammalian pituitary cell, comprising:

adding the prolactin lowering drug of claim 8 or claim 9, to the cell in an amount sufficient to lower the release of prolactin by the cell, compared to a control not receiving the prolactin lowering drug.

* * * * *